United States Patent
Zambianchi et al.

(10) Patent No.: US 12,337,084 B2
(45) Date of Patent: Jun. 24, 2025

(54) FILTER ASSEMBLY AND CONTAINER FOR COLLECTING BLOOD CONTAINING THE SAME

(71) Applicant: FRESENIUS HEMOCARE ITALIA S.R.L., Mirandola (IT)

(72) Inventors: Laura Zambianchi, Reggio Emilio (IT); Timo Matser, El De Wijk (NL); Giuseppe Antonio Mulas, Modena (IT); Paolo Verri, Capri (IT)

(73) Assignee: FRESENIUS HEMOCARE ITALIA S.R.L., Mirandola (IT)

( * ) Notice: Subject to any disclaimer, the term of this patent is extended or adjusted under 35 U.S.C. 154(b) by 84 days.

(21) Appl. No.: 17/252,824

(22) PCT Filed: Jun. 19, 2019

(86) PCT No.: PCT/EP2019/066239
§ 371 (c)(1),
(2) Date: Dec. 16, 2020

(87) PCT Pub. No.: WO2019/243439
PCT Pub. Date: Dec. 26, 2019

(65) Prior Publication Data
US 2021/0187176 A1 Jun. 24, 2021

(30) Foreign Application Priority Data
Jun. 20, 2018 (EP) .................................... 18178843

(51) Int. Cl.
*B01D 29/00* (2006.01)
*A61M 1/02* (2006.01)
(Continued)

(52) U.S. Cl.
CPC ......... *A61M 1/0281* (2013.01); *B01D 29/111* (2013.01); *B01D 29/23* (2013.01);
(Continued)

(58) Field of Classification Search
CPC ...... B01D 25/00; B01D 25/001; B01D 25/02; B01D 25/12; B01D 25/21; B01D 27/00;
(Continued)

(56) References Cited

U.S. PATENT DOCUMENTS

| 4,066,556 A | 1/1978 | Vaillancourt |
| 4,732,675 A * | 3/1988 | Badolato ................ B01D 29/56 55/501 |

(Continued)

FOREIGN PATENT DOCUMENTS

| CN | 101076338 A | 11/2007 |
| EP | 2495025 A1 | 9/2012 |

(Continued)

OTHER PUBLICATIONS

European Search Report of Dec. 6, 2018 for European Application No. 18178843.1.

(Continued)

*Primary Examiner* — Allison G Fitzsimmons
(74) *Attorney, Agent, or Firm* — Cook Alex Ltd.

(57) ABSTRACT

A filter assembly comprising a prefiltering support layer (84) is disclosed, wherein the prefiltering support layer (84) comprises a non-woven fabric of fibers, the non-woven fabric having a pore size. A first mesh filter layer (85) is arranged downstream the prefiltering support layer (84), wherein the first mesh filter layer (85) has a first mesh size, wherein the pore size of the prefiltering support layer (84) is equal to or bigger than the first mesh size of the first mesh filter layer (85). A container for collecting a body fluid comprising such a filter assembly as well as a method for manufacturing such a filter assembly are also disclosed.

13 Claims, 7 Drawing Sheets

(51) Int. Cl.
*B01D 29/11* (2006.01)
*B01D 29/23* (2006.01)
*B01D 39/16* (2006.01)
*B32B 5/02* (2006.01)
*B32B 5/26* (2006.01)
*B01D 39/00* (2006.01)

(52) U.S. Cl.
CPC ....... *B01D 29/232* (2013.01); *B01D 39/1623* (2013.01); *B32B 5/022* (2013.01); *B32B 5/26* (2013.01); *A61M 2205/7536* (2013.01); *A61M 2207/00* (2013.01); *B01D 2201/0415* (2013.01); *B01D 2201/18* (2013.01); *B01D 2201/204* (2013.01); *B01D 2239/0618* (2013.01); *B01D 2239/0627* (2013.01); *B01D 2239/0654* (2013.01); *B01D 2239/1216* (2013.01); *B32B 2250/20* (2013.01); *B32B 2307/726* (2013.01); *B32B 2535/00* (2013.01)

(58) Field of Classification Search
CPC ........ B01D 27/04; B01D 27/06; B01D 27/08; B01D 27/14; B01D 29/00; B01D 29/0002; B01D 29/0093; B01D 29/0095; B01D 29/01; B01D 29/012; B01D 29/05; B01D 29/03; B01D 29/035; B01D 29/07; B01D 29/071; B01D 29/073; B01D 29/11; B01D 29/111; B01D 29/13; B01D 29/50; B01D 29/56; B01D 29/58; B01D 39/00; B01D 39/08; B01D 39/086; B01D 39/10; B01D 39/12; B01D 39/14; B01D 39/16; B01D 39/1607; B01D 2201/29; B01D 2275/00; B01D 2275/10; B01D 2275/105; B01D 2275/206; B01D 2275/302; B01D 2275/305; B01D 2275/307; B01D 2325/00; B01D 2325/02; B01D 2325/021; B01D 2325/0283; B01D 36/1607; B01D 29/031; E02B 11/00; E02B 11/02; B31B 50/00; B31B 50/59; B31B 2120/00; B31B 2120/10; B31B 2120/20; B31B 2120/60; B31B 1/00; B31B 3/00; B31B 5/00; B31B 2439/00; B31B 2439/02; B31B 2439/40; B31B 2439/70; B31B 2553/00
See application file for complete search history.

(56) References Cited

U.S. PATENT DOCUMENTS

| | | | |
|---|---|---|---|
| 4,994,022 A | 2/1991 | Steffler et al. | |
| 5,258,127 A | 11/1993 | Gsell et al. | |
| 5,362,406 A * | 11/1994 | Gsell | B01D 39/1623 |
| | | | 210/508 |
| 6,441,125 B2 | 8/2002 | Bonte et al. | |
| 6,908,446 B2 | 6/2005 | Yokoyama et al. | |
| 7,736,516 B2 | 6/2010 | Zambianchi et al. | |
| 7,775,376 B2 | 8/2010 | Bonaguidi et al. | |
| 8,157,103 B2 | 4/2012 | Eagle et al. | |
| 8,597,417 B2 | 12/2013 | Kobayashi et al. | |
| 10,004,840 B2 | 6/2018 | Zambianchi et al. | |
| 10,238,786 B2 | 3/2019 | Ducoroy et al. | |
| 2002/0113003 A1 | 8/2002 | Lynn et al. | |
| 2003/0175151 A1 | 9/2003 | Ghelli et al. | |
| 2008/0314836 A1 | 12/2008 | Leach et al. | |
| 2010/0187712 A1* | 7/2010 | Gupta | D04H 1/4218 |
| | | | 264/103 |
| 2011/0180482 A1 | 7/2011 | Leach et al. | |
| 2011/0272343 A1 | 11/2011 | Gourlay et al. | |
| 2014/0299556 A1* | 10/2014 | Zambianchi | B01D 39/1623 |
| | | | 210/435 |
| 2016/0354530 A1* | 12/2016 | Peticca | A61M 1/3623 |
| 2017/0136167 A1 | 5/2017 | Verri et al. | |
| 2017/0151382 A1* | 6/2017 | Lynn | B01D 39/10 |
| 2017/0354774 A1 | 12/2017 | Lee et al. | |

FOREIGN PATENT DOCUMENTS

| | | | |
|---|---|---|---|
| GB | 1440027 A | | 6/1976 |
| JP | S 61-155012 U | | 7/1986 |
| JP | H 02-271868 A | | 11/1990 |
| JP | H 04-240456 A | | 8/1992 |
| JP | 2003-265605 A | | 9/2003 |
| JP | 2004339165 A | | 12/2004 |
| JP | 2010-88736 A | | 4/2010 |
| JP | 2010-531167 A | | 9/2010 |
| JP | 5587182 B2 | | 9/2014 |
| KR | 1020160081825 B1 | | 7/2016 |
| WO | 2016196584 A1 | | 12/2016 |

OTHER PUBLICATIONS

International Search Report and Written Opinion mailed on Oct. 11, 2019, for International Application No. PCT/EP2019/066239.
Japanese Search Report by Registered Search Organization dated Apr. 28, 2023 Japanese App. No. 2020-570708 with English translation.

* cited by examiner

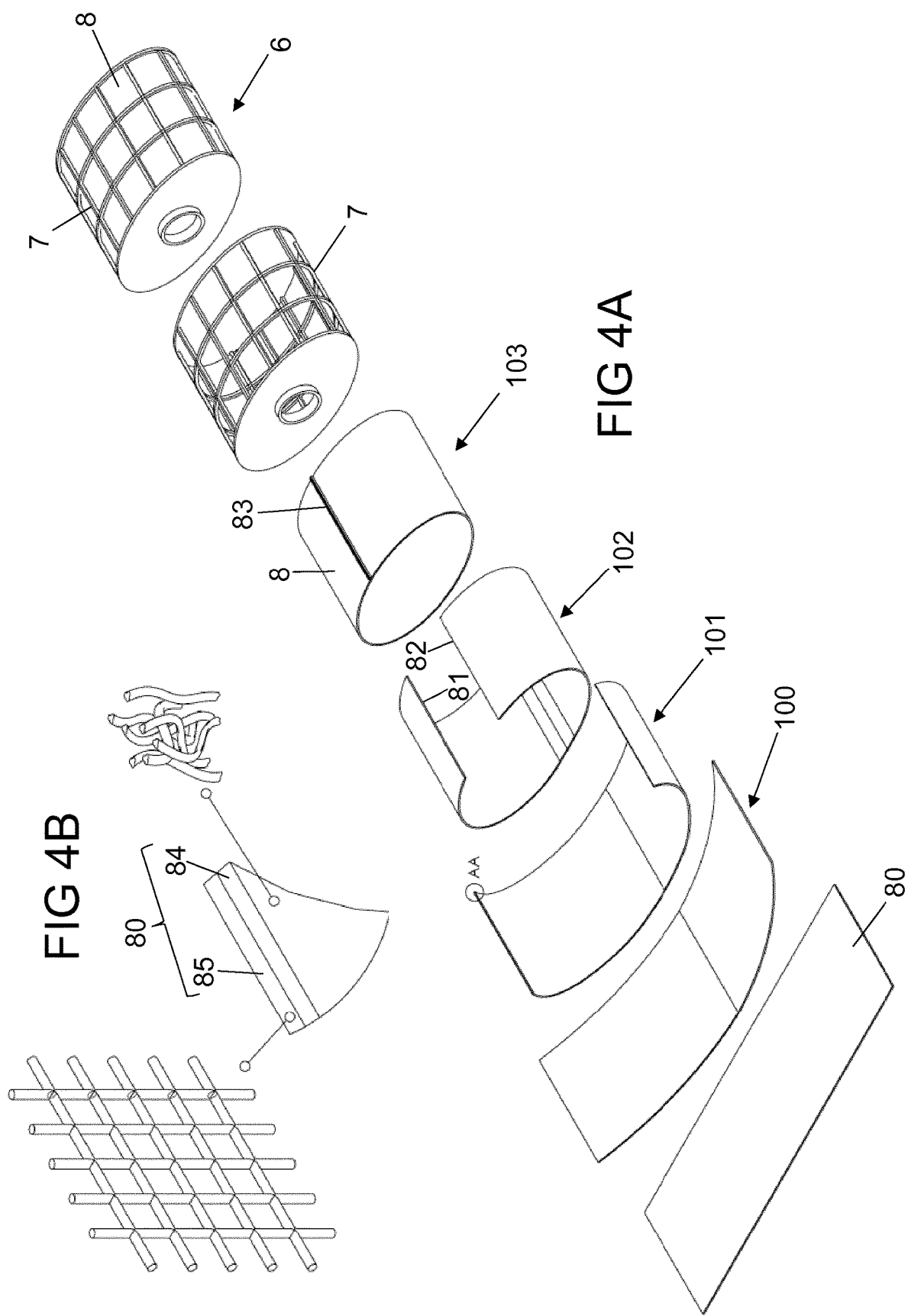

FILTER ASSEMBLY AND CONTAINER FOR COLLECTING BLOOD CONTAINING THE SAME

CROSS-REFERENCE TO RELATED APPLICATIONS

This application is the U.S. National Stage of International Application No. PCT/EP2019/066239, filed Jun. 19, 2019, which claims the benefit of and priority to European Application No. 18178843.1, filed Jun. 20, 2018 the contents of which are incorporated herein by reference.

The present invention relates to a filter assembly, to an appropriate use of such a filter assembly, to a container for collecting a body fluid comprising such filter assembly as well as to a method for manufacturing such a filter assembly.

DESCRIPTION

Filtering assemblies known from prior art are used to filter different types of fluids, e.g. body fluids, for removing aggregates, particles or specific cells from said fluids. A particular appropriate application of filter assemblies is the filtration of blood. Whole blood comprises three major cellular components, namely, red blood cells, leukocytes (also designated as white blood cells) and thrombocytes (also designated as platelets). A major non-cellular component of the blood is the blood plasma.

Whole blood or blood components may be separated and further processed for a variety of uses, particularly for use as transfusion products.

Filtering assemblies are also used in auto transfusion processes during surgeries procedures; i.e. blood of a patient is recovered during surgery and re-infused into the patient. This is also known as Intraoperative blood salvage, or autologous blood transfusion or cell salvage. It has been used for many years and gained greater attention over time as risks associated with allogenic (separate-donor) blood transfusion have seen greater publicity and become more fully appreciated. Several medical devices have been developed to assist in salvaging the patient's own blood in the perioperative setting. The procedure is frequently used in cardiothoracic and vascular surgery, during which blood usage has traditionally been high.

Whole blood recovered during surgery, but being exposed to surgery, air etc. has different characteristics than blood collected in a blood bank from a donor for allogeneic transfusion purpose. For example, blood salvage requires a removal of blood clots, non-cellular substances, such as drugs or fluids used during surgery, bone fragments and surgery debris.

Commercially available filters for blood filtration and for the depletion of leukocytes and/or thrombocytes from whole blood or blood components are made using membrane technology, fiber technology, or a combination thereof. WO 2013/110694 A1 describes a blood filter comprising first fibers having at least one groove extending in the longitudinal direction of the fiber.

Filtering shed blood typically results in a foam formation in the filtered blood. One approach to avoid foam formation in shed blood is the use of antifoam agents in reservoirs where shed blood is collected for autotransfusion or extracorporeal circulation. In the past polydimethylsiloxane (PDMS)—hydrophobed silica was widely used as antifoam. However, PDMS is leached into the blood, where it emulsifies. It is presumed that most of it will be found in the waste after the washing procedure, but it cannot excluded that part of it is found in the Red Cell Concentrate that is autotransfused to the patient. Even though PDMS-hydrophobed silica is non-toxic in particular silica was associated as a possible source for emboli due to capillaries blockage and postoperative deaths and is no longer used as antifoam. Thus, nowadays only PDMS without silica is used. The defoaming principle remains the same for PDMS, while the physical way of action, a silica particle that "breaks" the bubble is no longer applied for medical devices, but is still used in non-medical defoaming.

However, there is still a need for alternative antifoaming concepts.

It is a first object of the present invention to provide materials that allow a reduction of foam formation in filtered body fluids, such as shed blood, and at the same time reduce the risk of leaching chemicals into the filtered body fluid.

The filtering assemblies as for example described above are typically used in specific body fluid collecting containers, in particular blood-collecting containers.

These containers serve for collecting blood during a surgical intervention of a patient. Afterwards, the blood is processed (washed) in order to remove undesired components of the blood and to increase the concentration of red blood cells in the blood. After processing the blood, it can be auto-transfused to the patient to avoid the necessity of providing the patient with blood donations.

Prior art blood collection containers comprises a filter socket that is manually tied to the top cover of the container. Currently, there is no automation of this process possible, thus increasing the overall manufacturing costs for such a container. The filter material is treated with antifoam agents that reduce the risk of foam formation in the blood. However, these antifoam agents leach from the filter, into the blood and thus administered to the patient when auto-transfusing the blood to the patient (as described above).

Furthermore, due to the specific design of certain filters comprising several layers of nonwoven fabric obtained in some cases also by staple fibers, loose fibers of individual layers or chemical binders or lubricants used to entangle the fibers and create the nonwoven structure might be leached and might thus contaminate the collected blood.

Blood collecting containers known from prior art are typically connected to a device that protects an undesired overfill of the blood collecting container. Such an overflow protection device (trap) is the only non-reusable component of the whole appliance. Its use is mandatory. The overflow protection device must be assembled manually to the vacuum circuit by the operator after it has been cleaned and sterilized in the hospital prior to use. A typical overfill protection device is a 100-ml glass with an input and an output cannula, wherein a floating element is constrained in the output cannula. In case of overflow of blood from the blood collection container into a vacuum line connected to the blood collection container, blood is drawn into the glass. An increasing level of blood in the glass results in rising the floating element (swimmer) until it is so high that it obstructs the output cannula. Then, the vacuum that is used for drawing blood into the blood collection container is interrupted. In such a case, the surgery has to be interrupted and the blood collecting device, the overfill protection device and the connecting vacuum lines have to be replaced. The overflow protection device has to be cleaned and sterilized for further use. This may take as long as several minutes. Since blood collecting containers typically have a volume of at least 3 liters, such overfill events only occur in case of massive bleeding. Then, the medical staff is already likely to be stressed due to the critical situation of the patient. If in such circumstances additional work is necessary, the staff may decide to interrupt collection of intraoperatory shed blood for later autotransfusion and rely, if needed, on allogenic transfusions.

When collecting blood from a patient during surgery, typically a smoke filter is provided in the vacuum line that is used to create vacuum in the container and consequently in the cannula for drawing blood from the patient. This smoke filter serves for filtering surgical smoke and for preventing this smoke from clogging the antibacterial filter which protects the vacuum pump from surgical air contamination. Smoke filters known from prior art are stand-alone multi- or single-use disposables medical devices or accessories that are manually integrated into a vacuum line of the appliance serving for drawing blood from a patient.

Lastly, an antibacterial or antiviral filter is connected to the vacuum line and used to protect the pump from surgical air contamination. It is disposable and may be single- or multi-use. Single-use filters are typically integrated in the vacuum line.

It is a second object of the present invention to provide a body fluid collecting container, in particular a blood collecting container, that can be easier and cheaper manufactured than body fluid collecting containers known from prior art. Furthermore, the use of the body fluid collecting container shall be made easier than the use of body fluid collecting containers known from prior art.

The first and second objects are achieved by a filter assembly and a container for collecting a body fluid having the features explained in the following.

According to a first aspect of the invention a filter assembly is provided that comprises a prefiltering support layer. The prefiltering support layer in turn comprises or essentially consists of a non-woven fabric of fibers. Thereby, the fibers are arranged such that gaps are formed between the fibers. Consequently, an average pore size of the non-woven fabric (for depth filtration) results.

A first (woven) mesh filter layer (for surface filtration) is arranged downstream the prefiltering support layer, wherein the first mesh filter layer has a first mesh size, wherein the pore size of the prefiltering support layer is equal to or bigger than the first mesh size of the first mesh filter.

The terms "downstream" and "upstream" refer to a flow direction of a fluid to be filtered by the filter assembly. By such an arrangement, the prefiltering support layer does not alter or limit the filtration properties of the first mesh filter layer but mainly serves for stabilizing the first mesh filter layer and keeping the first mesh filter layer in place. Some of the particles that would have been filtered by the first mesh filter layer are already filtered by the prefiltering support layer, so that the filtration load of the first mesh filter layer is reduced. Thus, the prefiltering support layer does not only stabilize the first mesh filter layer, it also serves for avoiding a premature clogging of the first mesh filter layer.

The filter assembly further comprises a filter holder arranged downstream of the mesh filter layer. This filter holder contacts both the prefiltering support layer and the first mesh filter layer. In doing so, it also stabilizes the prefiltering support layer as well as the first mesh filter layer. Thus, the filter holder serves for keeping the prefiltering support layer and the first mesh filter layer in place; it acts as structural support. The filter assembly is a stand-alone filter assembly (self-sustained filter assembly) or it can be one part (overmoulded) with filter layers.

It was surprisingly found that such a filter assembly can well be used for filtering blood and other body fluids. If such a filter assembly is used, foam formation in the blood and in other body fluids is effectively prevented. Thereby, no anti-foaming agents are necessary so that the risk of leaching chemicals into the filtrated body fluid is fully avoided.

Using a filter assembly comprising a prefiltering support layer as well as a mesh filter layer instead of a regular filter (made only of fibers or foam or a membrane) is connected to the effect that extremely reproducible filtering conditions can be met. While regular filters have an average pore size with many pores being bigger or smaller than the average pore size, a mesh filter has a clearly defined mesh size that essentially does not vary. In order to processed, in particular a thin mesh with a lower mesh size needs a support that can be another open mesh or a continuous filament nonwoven material, such as a spunbond.

In an embodiment, the filter holder is made from plastic and is overmolded over a part of the prefiltering support layer and a part of the first mesh filter layer. Then, it tightly connects both layers together and serves particularly easy for a good stabilization of both layers.

In an embodiment, the prefiltering support layer and the first mesh layer are no separate components, but are rather integrally formed and thus build up a structural composite. "Structural composite" means that the prefiltering support layer and the first mesh filter layer can be made of the same material but do have a different structure (the prefiltering support layer is a non-woven fabric; the first mesh filter layer is a mesh or net).

In an embodiment, the first mesh layer is made of a plurality of interconnecting threads forming a screen or grid or a net. Thus, vertically arranged threads and horizontally arranged threads are connected to each other at connecting points so as to form a grid.

In an embodiment, the filter assembly comprises a second mesh filter layer. The second mesh filter layer has a second mesh size, wherein the second mesh size is equal to or bigger than the pore size of the prefiltering support layer. Thereby, the prefiltering support layer is arranged in between the first mesh filter layer and the second mesh filter layer. Thus, the first mesh filter layer, the prefiltering support layer and the second mesh filter layer are arranged in a sandwich-like manner, wherein the prefiltering support layer is encompassed by the first mesh filter layer and the second mesh filter layer; i.e. the downstream arrangement is in the order second mesh filter—filtering support layer—first mesh filter. Such an arrangement serves for a particularly stable arrangement of the mesh layers and thus for a particular stable filter assembly.

The filter holder is, in an embodiment, also overmolded over a part of the second mesh layer to also tightly connect this layer to the other two layers.

Prefiltering Support Layer

As mentioned above, the prefiltering support layer comprises or essentially consists of continuous filament spunbond nonwoven fabric. Said fabrics are obtained in continuous filament nonwoven processes (meltblowing and spunbonding) that start extruding chips or pellets of raw material. The length of the filament is theoretically infinite, thus lowering the risks of leaching fibers (as observed in needled felt nonwoven fabrics) is essentially lower than for needled felt materials.

In an embodiment the individual fibers of the prefiltering support fabric may have any desired cross-section, such as a circular, elliptic rectangular, quadratic or triangular cross-section. Mixtures of fibers having different cross sections are also possible.

The fibers of the prefiltering support layer can also generally have any shape. However, it turned out that particularly good filtering can be achieved if the fibers, or at least a part of the fibers, comprise at least one groove extending in the longitudinal direction of the respective fiber. To give an example, the fibers may comprise three grooves each extending in a longitudinal direction of the fiber. Then, aggregates, fat and/or platelets can be particularly well filter from blood or another body fluid flowing through the filter assembly.

In an embodiment, at least a part of the fibers has a lobate cross-section. Such a lobate cross-section can be achieved, in an embodiment, by forming a groove in the fibers in the longitudinal direction. A trilobal cross-section is a particularly well suited example of a lobate structure. Such trilobal fibers are generally known, e.g., from WO 2013/110694 A1, the entire content of which is hereby incorporated by reference.

The fibers making up the non-woven fabric of the prefiltering support layer can be, in an embodiment, spunbond fibers or melt-blown fibers. While spunbond fibers typically have a fiber diameter that is at least 20 µm or larger, melt-blown fibers may have lower diameters of less than 20 µm.

The fibers may be monocomponent, bicomponent or multicomponent fibers, including "island in the sea" fibers. The fibers may consist of one polymer or a blend of polymers. Suitable materials for the fibers are, for example, a polyester, polyethylene, polypropylene, polybutylene, polymethylpentene, polyethylene terephthalate, polytrimethylene terephthalate, polybutylene terephthalate, poly(butylene terephthalate-co-polyalkylene glycol terephthalate), nylon 6,6, nylon 6,9, nylon 6/12, nylon 11, nylon 12, cellulose acetate, cellulose acetate propionate, or a combination thereof. Thereby, a non-hydrophobic or hydrophilic material is particularly appropriate to produce the fibers. It is also possible to increase the hydrophilicity of the material which is used to produce the fibers or to increase the hydrophilicity of the already produced fibers. Thereby, a physical treatment is more appropriate than the deposition of chemicals because such chemicals might potentially be leached from the fibers or the fabric produced therefrom during use of the filter assembly.

In an embodiment, the pore size of the prefiltering support layer lies in a range of between 20 and 150 µm, in particular between 30 and 140 µm, in particular between 40 and 130 µm, in particular between 50 and 120 µm, in particular between 60 and 110 µm, in particular between 70 and 100 µm, in particular between 80 and 90 µm. Ranges of 100 to 130 µm, 105 to 125 µm, 70 to 90 µm, 75 to 85 µm, 30 to 45 µm and 35 to 40 µm are particularly appropriate.

First and Second Mesh Filter

In an embodiment, the first mesh filter layer can comprise or can be entirely made of a polymer such as a polyester, polyethylene, polypropylene, polybutylene, polymethylpentene, polyethylene terephthalate, polytrimethylene terephthalate, polybutylene terephthalate, poly(butylene terephthalate-co-polyalkylene glycol terephthalate), nylon 6,6, nylon 6,9, nylon 6/12, nylon 11, nylon 12, cellulose acetate, cellulose acetate propionate, or a combination thereof. Thereby, a non-hydrophobic or hydrophilic material is particularly appropriate to produce the mesh filter layer. It is also possible to increase the hydrophilicity of the material which is used to produce the mesh filter layer or to increase the hydrophilicity of the already produced filter. Thereby, a physical treatment is more appropriate than the deposition of chemicals because such chemicals might potentially be leached from the mesh filter during use of the container. An appropriate surface area of the mesh filter layer lies in a range of 300 to 1000 cm$^2$, in particular 400 to 900 cm$^2$, in particular 500 to 800 cm$^2$, in particular 600 to 700 cm$^2$.

In an embodiment, the mesh filter layer is made from the same material as the prefiltering support layer.

In another embodiment, the second mesh filter layer is, besides its mesh size, structurally identical to the first mesh filter layer. In such a case, the first mesh filter layer and the second mesh filter layer are structurally very similar. This facilitates manufacturing of the filtering assembly.

In an embodiment, the threads or filaments of the first mesh filter layer and/or the second mesh filter layer have a circular cross-section. However, other cross sections, such as an elliptic, a rectangular, a quadratic or a triangular cross-section would also be possible. Likewise, mixtures of threads or filaments having different cross sections are also possible.

In an embodiment, the first mesh size of the first mesh filter layer and/or the second mesh size of the second mesh filter layer lies in a range of between 20 and 150 µm, in particular between 30 and 140 µm, in particular between 40 and 130 µm, in particular between 50 and 120 µm, in particular between 60 and 110 µm, in particular between 70 and 100 µm, in particular between 80 and 90 µm. Ranges of 100 to 130 µm, 105 to 125 µm, 70 to 90 µm, 75 to 85 µm, 30 to 45 µm and 35 to 40 µm are particularly appropriate, for example 115 µm, 120 µm or 40 µm.

In an embodiment, the non-woven fabric of the prefiltering support layer has areas of different pore size. This enables the prefiltering support layer to have at least two zones with different filtration capacities. To give an example, a first zone of the prefiltering support layer might have a poresize lying in a range of 20 µm to 60 µm, in particular of 25 µm to 55 µm, in particular of 30 µm to 50 µm, in particular of 35 µm to 45 µm, in particular of 38 µm to 42 µm, i.e., around 40 µm. In an embodiment, the pore size of the first area is 40 µm. The second area has a different pore size than the first area. The pore size of the second area lies, in an embodiment, in a range of 60 µm and 120 µm, in particular of 65 µm to 95 µm, in particular of 70 µm to 90 µm, in particular of 75 µm to 85 µm, in particular of 78 µm to 82 µm, i.e. around 80 µm. In an embodiment, the pore size of the second area is 80 µm.

In another embodiment, the prefiltering support layer has three zones or areas of different filtration capacities due to different pore sizes of the non-woven fabric.

Thus, in an embodiment, the first and second area as explained with respect to the preceding embodiment might be combined with a third area that has a pore size differing from the pore sizes of the first and second area. Thereby, the pore size of the third area lies, in this embodiment, in a range of 100 µm to 140 µm, in particular of 105 µm to 135 µm, in particular of 110 µm to 130 µm, in particular of 115 µm to 125 µm, in particular of 118 µm to 122 µm, i.e. around 120 µm. In an embodiment, the pore size of the third area is 120 µm.

The arrangement of at least three different pore size areas in the prefiltering support layer provides a pore size gradient. In one example the gradient starts with a pore size of 40 µm in the first area, followed by a pore size of 80 µm in the second area and a pore size of 120 µm in the third area. In this case the pore size gradient is a stepwise gradient of the pore size. Any combination of pore sizes in such a stepwise gradient are conceivable.

The first mesh filter layer and/or the second mesh filter layer may likewise have different areas of mesh sizes, e.g., areas as explained above with respect to the prefiltering support layer.

Thus, in an embodiment, the areas (or gradient) of different mesh sizes are formed by establishing a gradient of mesh size within the non-woven fabric of the prefiltering support layer or within the mesh of the first mesh filter layer and/or the second mesh filter layer, respectively.

In an embodiment, the prefiltering support layer, the first mesh filter layer and optionally a second mesh filter layer extend over a vertical extension direction and over a horizontal extension direction. Thereby, the vertical extension direction is vertically aligned during normal operation of the filter assembly. Likewise, the horizontal extension direction is horizontally aligned during normal operation of the filter assembly. The non-woven fabric of the prefiltering support layer and/or the first mesh filter layer and/or the second mesh filter layer (if present) has a first area in a first height of the vertical extension direction and a second area in a second height of the vertical extension direction. The second height differs from the first height. The first area and the second area have different mesh sizes and exhibit different filtration capacities. Consequently, the filter assembly has a vertical gradient of filtration capacity. Thereby, the lowest area typically has the lowest filtration capacity (it allows the lowest flow rate) but has the highest filtration performance (it filters the smallest particles). Likewise, the topmost area typically has the highest filtration capacity but has the lowest filtration performance. Intermediate areas typically have intermediate filtration capacities and performances.

The exemplary pore sizes and mesh sizes indicated above are explicitly appropriate for the previously explained embodiment.

In an embodiment, the filter assembly does not comprise any anti-foaming agents. By avoiding the use of such anti-foaming agents the risk of leaching anti-foam chemicals into a fluid that is flowing through the filter assembly is fully prevented. This enhances the quality of the fluid filtered by the filter assembly.

The present invention relates in an aspect to the use of the filter assembly having the features explained above for filtering a body fluid in vitro. Thereby, the body fluid can be blood, urine, bile, tissue fluid, sperm, lymph, saliva or cerebrospinal fluid. Blood is a particularly appropriate body fluid to be filtered.

In an aspect, the present invention relates to a method of filtering a body fluid by letting the body fluid flow through a filter assembly according to the preceding explanations. The flow of the body fluid can be accomplished by gravity or by applying external forces such as low pressure to the body fluid or a container into which the filter body fluid is to be drawn. This method can be done in vitro or ex vivo, while a patient donating the body fluid to be filtered is connected to a filter appliance in which the body fluid is filtered. In an embodiment, the method is a medical method for drawing intraoperative cell salvage (ICS) from a patient in need thereof. ICS is typically used for patients undergoing surgery or invasive procedures and is intended to provide those patients with an autotransfusion of blood or blood components. More details on such a method are given in subsequent sections.

In an aspect, the present invention relates to a container for collecting a body fluid. Such a container comprises a container housing with a body fluid inlet that allows a body fluid to enter an inlet section of the container housing. The container housing furthermore comprises a body fluid collection section and a vacuum connector for connecting a vacuum source to the container housing. In doing so, a negative pressure can be applied to the inlet section and to the body fluid collection section. Thereby, the vacuum source is typically connected via a vacuum line to the vacuum connector of the container housing.

Furthermore, the container housing comprises a filter module that separates the inlet section from the body fluid collection section. To be more specific, the filter module is arranged between the inlet section and the body fluid collection section so that a body fluid needs to pass the filter in order to flow from the inlet section to the body fluid collection section. Expressed in other words, the filter module has a raw side and a clean side. The raw side faces the inlet section and the clean side faces the body fluid collection section.

The filter module additionally comprises a filter assembly according to the preceding explanations. Thereby, the filter assembly is arranged within the filter holder. Thus, the filter holder serves for supporting the filter assembly on the downstream side of the filter assembly. Such an arrangement is particularly appropriate for stabilizing the mesh filter of the filter assembly both from the upstream side (where the mesh filter layer is stabilized by the prefiltering support layer) and from the downstream side (where the mesh filter layer is stabilized by the filter holder). It is furthermore particularly appropriate for achieving a foam-free filtration of a body fluid such as blood.

In an embodiment, the container housing comprises a hydrophobic filter that is arranged between the body fluid collection section and the vacuum connector. Thereby, the term "between" relates to a flow direction of air drawn by a vacuum source from the container (or the body fluid collection section of the container housing) during the intended operation of the container. I.e., any fluid that is drawn from the interior of the container housing (in particular air and smoke) needs to pass the hydrophobic filter prior to entering a vacuum line connected to the vacuum connector. Thus, the hydrophobic filter serves as protective element for a vacuum line being connected to the vacuum connector of the container housing, when vacuum is generated by a vacuum pump.

The novel filter module and the hydrophobic filter synergistically act together so that this combination results in the effects explained in the following. By constructing the filter module with a filter holder and a filter assembly comprising a prefiltering support layer as well as a mesh filter layer, much more flexibility is given for the design of the filter holder than in case of using prefabricated filter sockets like in prior art. Furthermore, it is possible to manufacture the filter holder together with the filter assembly in a single manufacturing step, and the connection of the co-molded filter assembly component to the container is easily automatable. This significantly reduces manufacturing costs and increases the performance of the container due to more reliable and reproducible manufacturing steps. It further improves safety by streamlining the circuit that the user has to manually connect, thus preventing error of use (see IEC 62366-1:2015 and FDA Guidance Applying Human Factors and Usability Engineering to Medical Devices Guidance for Industry and Food and Drug Administration Staff, Document issued on: Feb. 3, 2016).

The hydrophobic filter arranged in flow direction before the vacuum connector serves both as smoke filter and as overfill protection. Thus, it combines the properties of these elements, which are used in form of individual components according to prior art, in a single element. This single element is thereby included in the container housing. Thus, it is not necessary to connect it with a separate vacuum line. There is no need to clean and/or sterilize the hydrophobic filter. Rather, it can be designed as disposable that is discarded together with the whole container. This additionally facilitates the use of the container.

In an embodiment, a top cover or an inlet section of the container housing and the filter holder are manufactured as one piece, i.e., they are integrally formed. This facilitates the manufacturing steps significantly since no manual attachment of a filter to the container housing is necessary anymore. To give an example, the filter holder and (at least parts of) the container housing can be co-molded in one single injection molding step. Then, an outlet of the inlet section of the container housing turns integrally into an inlet of an interior of the filter holder. Any body fluid that enters the inlet section will then flow or will be drawn from the inlet section of the container housing towards an interior space of the filter holder. It has then to pass the filter assembly in order to reach the body fluid collection section.

In an embodiment, the filter holder and the filter assembly are free of antifoam agents. While certain antifoam agents are necessary in case of regular filters to avoid an undesired foaming of blood, the design of the blood path through the filter element tend to induce foam formation in blood only to a very low extent. If no antifoam agents are used, no such agents can be leached into body fluids so that no corresponding contamination of the body fluid needs to be feared.

In an embodiment, the filter holder comprises bars or struts that stabilize the filter material which is located in an interior of the filter holder. Such bars can be easily produced by injection molding, e.g., directly on the filter material. They prevent the filter material to collapse and to stick wet. Furthermore, they can be used during injection molding to carry molten plastics to create a punt at the bottom of the filter element.

In an embodiment, an inlet area of the filter module is funnel-shaped. Such a funnel shape reduces the risk of foam formation in the body fluid. Thus, the funnel shape of the inlet area can also be considered as part of the concept "defoaming by design" that is, in an embodiment, applied to the filter module. Thereby, typically the filter holder has this specific funnel-shaped inlet area, whereas the filter assembly does not need to have any specific design (as long as it fits into the filter holder).

In an embodiment, the bottom of the filter module is not entirely flat, but rather comprises an indention towards an interior space of the filter module. Thereby, this indention extends, in an embodiment, over essentially the full area of the bottom of the filter module (in particular of the filter holder). Then, the bottom of the filter module has a concave shape when looked from the outside of the filter module and a convex shape when looked from the inside of the filter module. Such a design of the bottom of the filter module plays also a role in the "defoaming by design" approach taken in an embodiment. The indention of the bottom of the filter module can also be described as a shape like a champagne's bottle punt. This shape avoids spurts of body fluid passing through the filter module and reduces the falling height of the body fluid passing through the filter module. The lower the falling height, the lower the risk of foam formation in the body fluid.

In an embodiment, the hydrophobic filter is integrated into the top cover of the container housing. Then, it is arranged in an upper location of the container so that the risk of getting into contact with the body fluid is significantly reduced. Furthermore, such integration in the top cover of the container still allows a compact design of the whole container.

The hydrophobic filter comprises, in an embodiment, a filter housing and a filter material placed in the filter housing. While it would be generally possible to design the hydrophobic filter as exchangeable element, it is intended, in an embodiment, that the hydrophobic filter is a disposable element that is discarded together with the whole body fluid collecting container. The lifetime of the hydrophobic filter is generally longer than the lifetime of the body fluid collecting container so that it is generally not necessary to replace the hydrophobic filter during the intended operation of the body fluid collecting container.

The hydrophobic filter may also be a mesh filter, wherein a mesh size of 1 to 20 µm, in particular 3 to 19 µm, in particular 4 to 18 µm, in particular 5 to 17 µm, in particular 6 to 16 µm, in particular 7 to 15 µm, in particular 8 to 14 µm, in particular 9 to 13 µm, in particular 10 to 12 µm is appropriate.

The hydrophobic filter is intended to filter air drawn by a vacuum source from the container for collecting a body fluid, or, to be more precisely, from the body fluid collecting section of this container. The hydrophobic filter protects the vacuum source from smoke (in particular surgical smoke), particles (such as bone or tissue fragments), and blood and also reduces the load of contaminations of the hydrophobic antibacterial filter that is associated to the pump and thus located downstream from the hydrophobic filter.

In an embodiment, the hydrophobic filter comprises a filter material comprising or consisting of a hydrophobic polymer such as polytetrafluoroethylene (PTFE), in particular expanded PTFE (ePTFE).

In an embodiment, the hydrophobic filter comprises a filter material comprising or consisting of a non-hydrophobic polymer such as polyester (such as PET) treated with a hydrophobic polymer, in particular a hydrophobic PET mesh. Since the contact with blood of this element is occasional and very limited in time (spurts) and due to the position (top cover), the risk that the hydrophobic treatment is leached into the blood is minimal. However, the hydrophobic treatment has to be biocompatible.

In an embodiment, the hydrophobic filter comprises a pleated filter material. By pleating the filter material, the effective filter surface can be increased while not increasing the overall space needed for the hydrophobic filter.

In an embodiment, the pleated filter material has a filter surface area being at least 3 times, in particular at least 4 times, in particular at least 5 times, in particular at least 6 times in particular at least 7 times, in particular at least 8 times as high as the surface area of the filter element that houses the hydrophobic filter. The filter surface area might be 3 to 8 times, in particular 4 to 7 times, in particular 5 to 6 as high as the surface area of the filter element that houses the hydrophobic filter. E.g., if the filter element has a surface area of 5 to 20 cm$^2$, the total filter surface might be in a range of 15 to 160 cm$^2$. Thus, by such an arrangement it is possible to incorporate a quite big filter surface area in a filter element that has only very low space requirements. This facilitates incorporating the hydrophobic filter into the top cover of the container housing while not increasing the dimensions of the top cover as compared to the top covers known from prior art.

In an embodiment, the container is specifically adapted to receive blood as body fluid. I.e., the body fluid referred to in the present description is, in this embodiment, blood.

The less foam formation in the collected body fluid, the better quality or higher yield of the collective body fluid is achieved. In case of blood as body fluid, lower foam formation results in lower hemolysis and lower platelets activation which in turn result in a higher blood recovery and better quality from the individual shed-blood processing steps. Mechanical stress of red blood cells is one ground of hemolysis.

Foam formation may be an indicator of biological stress.

In an aspect, the invention relates to a body fluid collecting arrangement comprising a vacuum source and a container according to the preceding explanations. Thereby, the vacuum source is directly connected to a vacuum connector of the container via a vacuum line. No component parts other than the vacuum line is present between the vacuum source and the container.

Body fluid collecting arrangements known from prior art have the following general setup: body fluid collecting container—vacuum line—overfill protection—smoke connector—smoke filter—vacuum line—vacuum pump. Thus, six connection points need to be established in total. If the vacuum source is directly connected to the connector like in the currently discussed aspect of the present invention, only two connection points need to be established: body fluid collecting container—vacuum line—vacuum source. Thus, the integration of the hydrophobic filter into the container housing of the body fluid collecting container renders a separate overflow protection, a separate smoke connector and a separate smoke filter superfluous. Three separate parts each having two connecting points can be fully skipped when relying on this aspect of the present invention. This significantly reduces the workload for medical staff preparing a body fluid collecting arrangement ready to be used.

In case of massive overflow of the body fluid collecting section of the container housing, it might happen that the collected body fluid passes through the hydrophobic filter. Then, the body fluid might enter the vacuum line that is connected to the vacuum connector of the container housing. In an embodiment, the vacuum line comprises a very hydrophobic antibacterial filter to protect the pump. Then, such overflow of small amounts of body fluids will not have any consequences. Rather, some hydrophobic vacuum lines are able to keep working also in the presence of accumulation of contaminations or liquids. The guiding principle, is to reduce complexity of assembly of the vacuum line to enhance usability.

In an embodiment, the vacuum line comprises an integrally formed antibacterial filter. Thus, this antibacterial filter does not represent an additional component part, but rather is an integral part of the vacuum line.

In an embodiment, the antibacterial filter is a hydrophobic filter. Then, it can also be used to effectively prevent any liquid that has entered the vacuum line, e.g., due to overfill events of the body fluid collection section of the container housing, from entering into the pump being arranged downstream of the antibacterial filter. It is possible to equip such an antibacterial filter with an additional chamber to accommodate any contaminations of the filter. Then, such chamber can also serve for receiving excessive body fluid drawn through the vacuum line due to an overfill event.

In an embodiment, the antibacterial filter has a pore size or mesh size that is sufficiently small to also filter viruses out of the fluid (in particular air) drawn through the vacuum line. In such a case, the antibacterial filter has also anti-viral properties. Then, it can be denoted as anti-viral filter.

In an aspect, the present invention relates to a method for manufacturing a container according to the preceding explanations. Thereby, a top cover of a container housing of the container and a filter holder of the container are co-molded, i.e., they are manufactured as one piece or, expressed in other words, they are integrally formed or integrally molded. Such a manufacturing process is significantly easier than the manufacturing processes known from prior art. It combines the previous method steps of producing a container housing and subsequently attaching a filter into the container housing into one single manufacturing step, namely a co-molding step. It can be accomplished, e.g., by injection molding.

While it is also possible to co-mold the filter assembly together with the filter holder, other approaches are taken in an embodiment of the manufacturing method. To be more precisely, in this embodiment, the filter assembly is applied (e.g., by molding) into the filter holder after the filter holder has been produced. Thereby, the filter holder itself may be co-molded with the top cover of the container housing. In doing so, it is not necessary to produce different molds for different mesh sizes to be applied for a filter module of the container housing. Rather, in this embodiment, only a single mold is necessary to produce a large number of container housing top covers with an integrally formed filter holder, wherein afterwards different filter assemblies filters can be applied into the filter holder, thus resulting in container housing top covers providing different filter properties (in particular different mesh sizes of the filter assembly).

In an aspect, the present invention relates to medical method for drawing intraoperative cell salvage (ICS) from a patient in need thereof. ICS is typically used for patients undergoing surgery or invasive procedures and is intended to provide those patients with an autotransfusion of blood or blood components. This method comprises the steps explained in the following. First, a blood suction line is connected to a blood inlet of a container for collecting blood. Furthermore, vacuum line is connected to a vacuum connector of this container and to a vacuum source, such as a vacuum pump. In doing so, a low pressure can be applied to an interior of the container, when the vacuum source is activated. The container is a container according to the preceding explanations. Thus, it comprises a container housing with the blood inlet that allows blood to enter an inlet section of the container housing. The container housing furthermore comprises a blood collection section. Thereby, the vacuum source is typically connected via a vacuum line to the vacuum connector of the container housing.

Furthermore, the container housing comprises a filter module that separates the inlet section from the blood collection section. To be more specific, the filter module is arranged between the inlet section and the blood collection section so that the blood drawn from the patient needs to pass the filter in order to flow from the inlet section to the blood collection section. Expressed in other words, the filter module has a raw side and a clean side. The raw side faces the inlet section and the clean side faces the blood collection section.

If all elements are assembled, the vacuum source is activated. Then, blood is drawn from a patient (e.g., during a surgical intervention) through the blood suction line into the receiving section of the blood-collecting canister. It then passes the filter and reaches the blood-collecting section. Afterwards, it can be drawn from the blood-collecting container in order to be further processed and/or autotransfused to the patient.

In an aspect, the present invention relates to a method for manufacturing a filter assembly according to the preceding explanations. As already mentioned, such a filter assembly comprises a filter holder, mesh filter layer and a prefiltering support layer. The prefiltering support layer comprises a non-woven fabric of fibers. Thereby, the non-woven fabric has a first mesh size. The filter holder is arranged downstream the first mesh filter layer. The first mesh filter layer, in turn, is arranged downstream of the prefiltering support layer. The first mesh filter layer has a second mesh size, wherein the first mesh size is equal to or bigger than the second mesh size.

The method is characterized in that the that the filter holder (which is made from plastic) is overmolded over a part of the prefiltering support layer and a part of the first mesh filter layer so that it contacts and stabilizes both the prefiltering support layer and the first mesh filter layer. Thus, only a single manufacturing step is necessary in order to place the filter holder around the two layers of filter material since it is manufactured in situ. This significantly facilitates the manufacturing of the filtering assembly as compared to filtering devices known from prior art. The filter holder can also form the ground area of the filter assembly. Thus, it may form the base of the filter assembly and at the same time embeds the filter material layers near the base to fix them.

In an embodiment, the first mesh filter layer and the prefiltering support layer initially form a flat ribbon. This flat ribbon is then brought into the desired shape of the filter assembly. This desired shape can be, e.g., the shape of a cylinder jacket, wherein the cylinder has a circular ground area, an elliptic ground area, a rectangular ground area or a quadratic ground area. The free ends of the shaped ribbon are then connected to each other. The connection of the free ends of the shaped ribbon can be accomplished, in an embodiment, by a welding process. Alternatively, the connection can be formed as a non-welded joint. The given shape is fixed by partially overmolding the prefiltering support layer and the first mesh filter layer with the filter holder. This manufacturing method of a filter assembly according to an aspect of the present invention is significantly easier than manufacturing techniques applied according to prior art. To be more precise, in prior art regularly a tubular filter arrangement made of two welded ribbons needs to be cut. The according manufacturing steps are significantly more difficult and increase the risk of particle contamination since welding and cutting two tubular ribbons may generate particulates that can be leached into a fluid that passes the filter.

All embodiments of the described filter assembly can be combined in any desired way and can be transferred to the described use, the described container for collecting a body fluid and the described methods, and vice versa in each case.

Further details of aspects of the present invention will be explained in the following with respect to exemplary embodiments and accompanying Figures. In the Figures:

FIG. 4A is a schematic depiction of a manufacturing process of an embodiment of a filter assembly;

FIG. 4B is an enlarged detailed view of the area in FIG. 4A that is encircled and marked with the letters AA;

Figure 1:
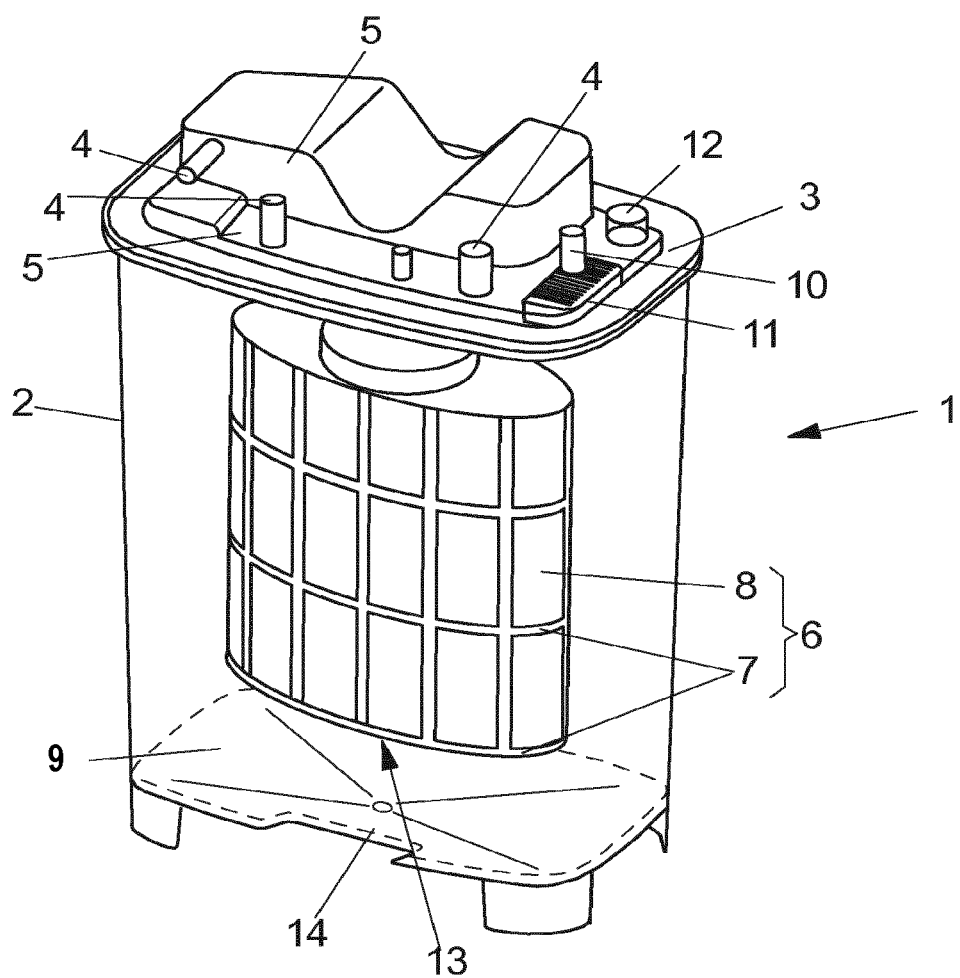
FIG. 1 is a perspective view of an embodiment of a blood-collecting canister.

FIG. 1 is perspective view of a blood-collecting canister 1 that serves as container for collecting a body fluid. The blood-collecting canister 1 comprises a canister housing 2 having a top cover 3. Three different blood inlets 4 are arranged in the top cover 3. Typically, only one of these blood inlets 4 is used for connecting a blood suction line with the blood-collecting canister 1 in order to draw blood from a patient into the interior of the canister housing 2. The most right blood inlet 4 is designed as a ⅜ inch connection. The middle blood inlet 4 is designed as Luer inlet, wherein the most left blood inlet 4 is designed as suction line connector sized for accommodating typical blood suction lines.

Each of the blood inlets 4 is fluidly connected with a blood receiving section 5 that is arranged on an inner side of the top cover 3. This blood receiving section 5 is in fluid communication with an interior of a filter module 6 (serving as filter assembly) that comprises a skeletal structure 7 that serves as filter holder. Inside the skeletal structure 7, two layers of filter material 8 are arranged. The filter material 8 comprises a prefiltering support layer as well as a mesh filter layer made of a medical grade mesh. If blood enters through the blood inlet 4 into the receiving section 5 of the blood-collecting canister 1, it flows or it is drawn into the interior of the filter module 6. Afterwards, it passes the filter material 8 and reaches a blood collection section 9 of the canister housing 2.

The blood-collecting canister 1 comprises in the top section 3 of the canister housing 2 a vacuum connector 10 that is intended to be connected to a vacuum line and, via the vacuum line, with a vacuum pump that serves as vacuum source. Air or any other gases being present in the blood-collecting section 9 that are drawn through the vacuum connector 10 into a connected vacuum line need to pass a hydrophobic filter 11 that is arranged between the blood-collecting section 9 and the vacuum connector 10.

The blood-collecting canister 1 further comprises a safety valve 12 that limits the amount of negative pressure that can be achieved within the interior of the canister housing 2. Thus, the safety valve 12 serves for reducing the risk of the blood-collecting canister 1 to implode due to an undesired low negative pressure in the interior of the canister housing 2.

When seen from the outside, a bottom 13 of the filter module 6 has a concave shape, i.e., it comprises an indention towards the interior of the filter module 6.

Blood that has entered the canister housing 2 through the blood inlet 4 and has passed the filter material 8 collects in the blood-collecting section 9. It can then be drawn through a blood outlet 14 out of the blood-collecting canister 1 in order to be further processed and/or auto-transfused to the patient.

Figure 2:
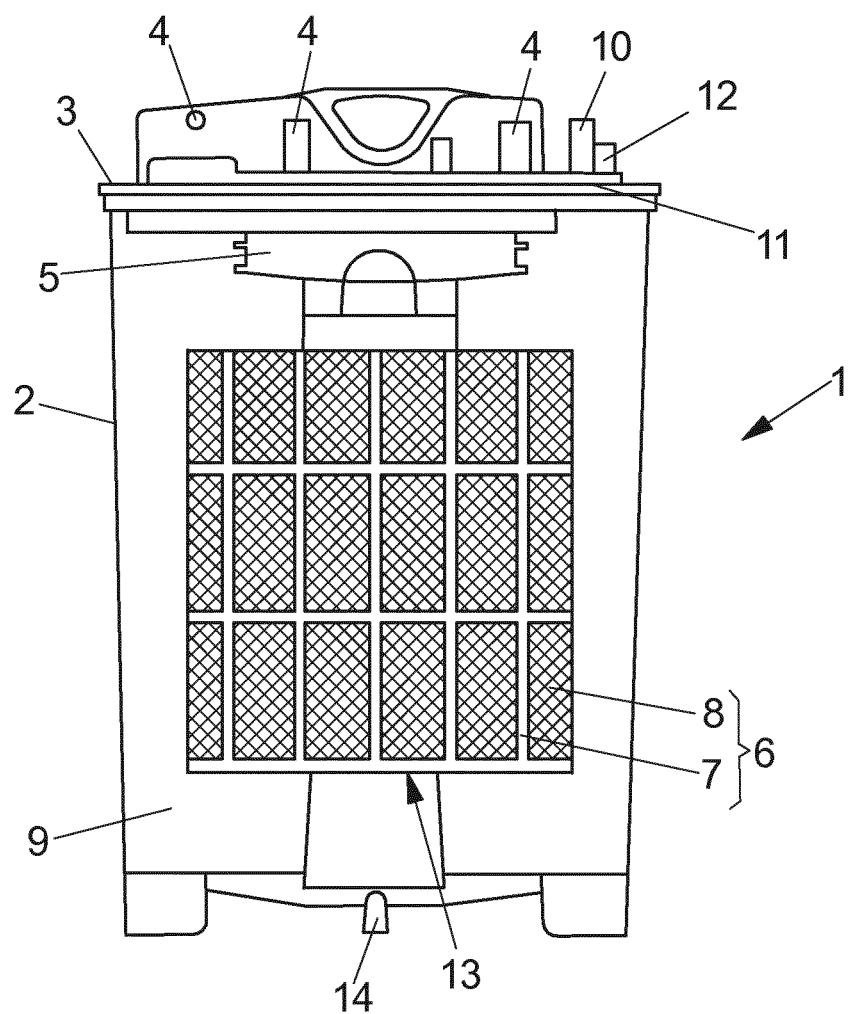
FIG. 2 is a side view onto the broad side of the canister of FIG. 1.

FIG. 2 shows the blood-collecting canister 1 from FIG. 1 in a side view onto the broad side of the blood-collecting canister 1. Thereby, the same numeral references for the same elements are used. Reference is made to the explanations given with respect to FIG. 1. In FIG. 2, a connection between the filter module 6 and the blood receiving section 5 of the canister housing 2 can be seen. It is apparent from FIG. 2 that blood can enter from the blood receiving section 5 only the interior of the filter module 6 and then needs to pass the filter material 8 in order to reach the blood-collecting section 9 of the canister housing 2. Thus, the filter module 6 separates the blood receiving section 5 from the blood-collecting section 9.

Figure 3:
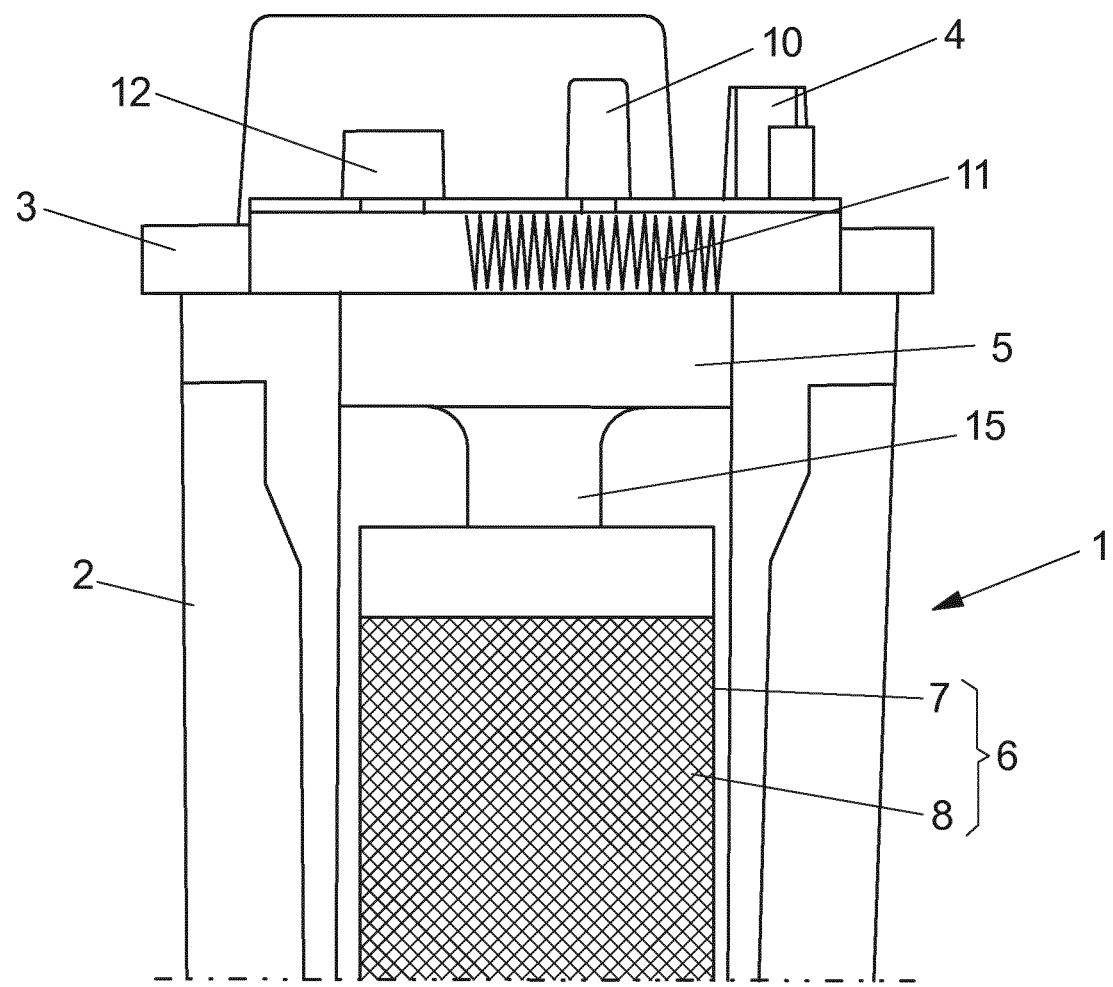
FIG. 3 is a detailed view of an upper part of the canister of FIG. 1 seen from the narrow side of the canister.

FIG. 3 shows a partially cut view from the narrow side onto the blood-collecting canister 1 of FIG. 1. Thereby, once again the same numeral references are used for the same elements. Reference is made once again to the explanations given above.

In the depiction of FIG. 3, a funnel-shaped inlet 15 is arranged in an inlet area of the filter element can be seen. Blood entering the filter module 6 from the blood receiving section 5 needs to pass needs to pass this funnel-shaped inlet 15. The funnel-shaped inlet 15 serves—together with the filter material 8 and the concavely shaped bottom 13 of the filter module 6 for a reduced foam formation in the blood that passes through the filter module 6. Such a reduced formation of foam leads to blood having better quality than foamed blood and to a higher collection yield due to a lower hemolysis rate.

It can be furthermore seen in the depiction of FIG. 3 that the hydrophobic filter 11 comprises a pleated filter material. Due to this folding of the filter material, the effective filter surface area is significantly increased. To give an example, the filter material of the hydrophobic filter 11 has an overall filter surface area of approximately 60 cm$^2$. Thereby, the hydrophobic filter itself takes only approximately 10 cm$^2$ space in the top cover 3 of the canister housing 2. Thus, by folding the filter material, the effective filter surface area is made six times as big as the surface area needed by the hydrophobic filter element 11.

FIG. 4A shows an exemplary manufacturing process of a filter module 6 that can be used as filter module for the blood-collecting canister shown in FIG. 1. First, a flat ribbon 80 of a co-molded spunbond prefilter (serving as prefiltering support layer) and a mesh filter (serving as mesh filter layer) is provided. This flat ribbon 80 is shaped into the desired shape in subsequent manufacturing steps 100, 101, 102 and 103. Thereby, the flat ribbon 80 becomes shaped filter material 8 that has, in this embodiment, the shape of a cylinder jacket with an elliptical ground area. Thereby, free ends 81 and 82 of the ribbon that are not yet connected in manufacturing step 102 are connected to each other to form a connection line 83 in manufacturing step 103. The connection line 83 can be realized in form of seam like a welded seam or in form of a seamless joint, i.e., a non-welded joint.

Speaking generally, this filter material 8 can then be inserted into a skeletal structure 7 of the bare filter module 6 so as to form a complete filter module 6 including the filter material 8. However, in an embodiment, the skeletal structure 7 is overmolded over the shaped filter material, e.g., by injection molding. Thereby, it partly embeds the individual layers of the shaped filter material (in particular at their bottom portion that is oriented towards the elliptical ground area) and serves for connecting them tightly together. Thereby, the skeletal structure can also overmold a seamless joint between the free ends of the shaped filter material 8 to also serve for a tight connection of the shaped filter material 8 between its free ends (i.e., along a vertical extension direction that is vertically aligned during normal operation of the assembled filter module 6).

FIG. 4B shows an enlarged detailed view of the area of the ribbon 80 that is encircled and marked with the letters AA in step 101 of FIG. 4A. This enlarged view shows that the ribbon 80 is made up of a prefiltering support layer 84 and a mesh filter layer 85. The structure of these two layers 84, 85 is also schematically depicted in FIG. 4B. Whereas the prefiltering support layer 84 consists of non-woven fibers with a trilobal cross-section, the mesh filter layer 85 consists of a regularly formed medical grade mesh.

Figure 5A:
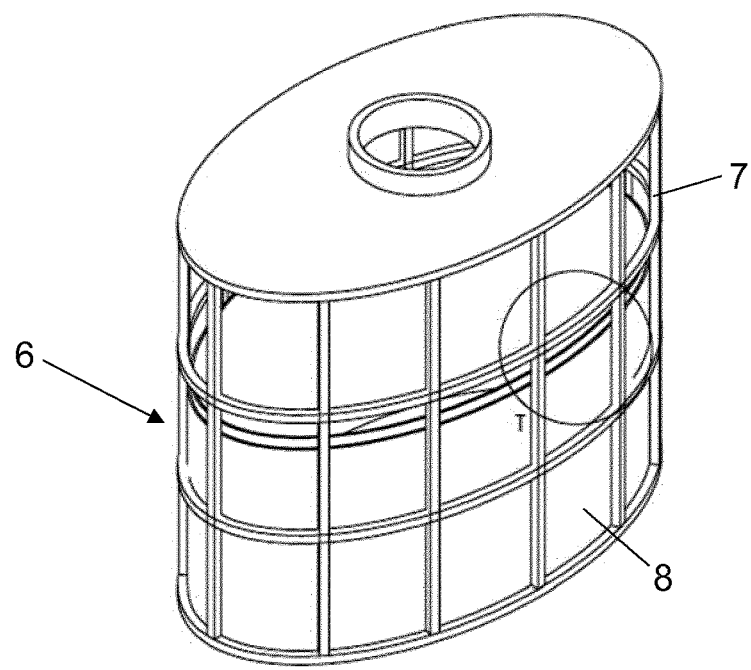
FIG. 5A is a partially cut depiction of another embodiment of a filter assembly.
Figure 5B:
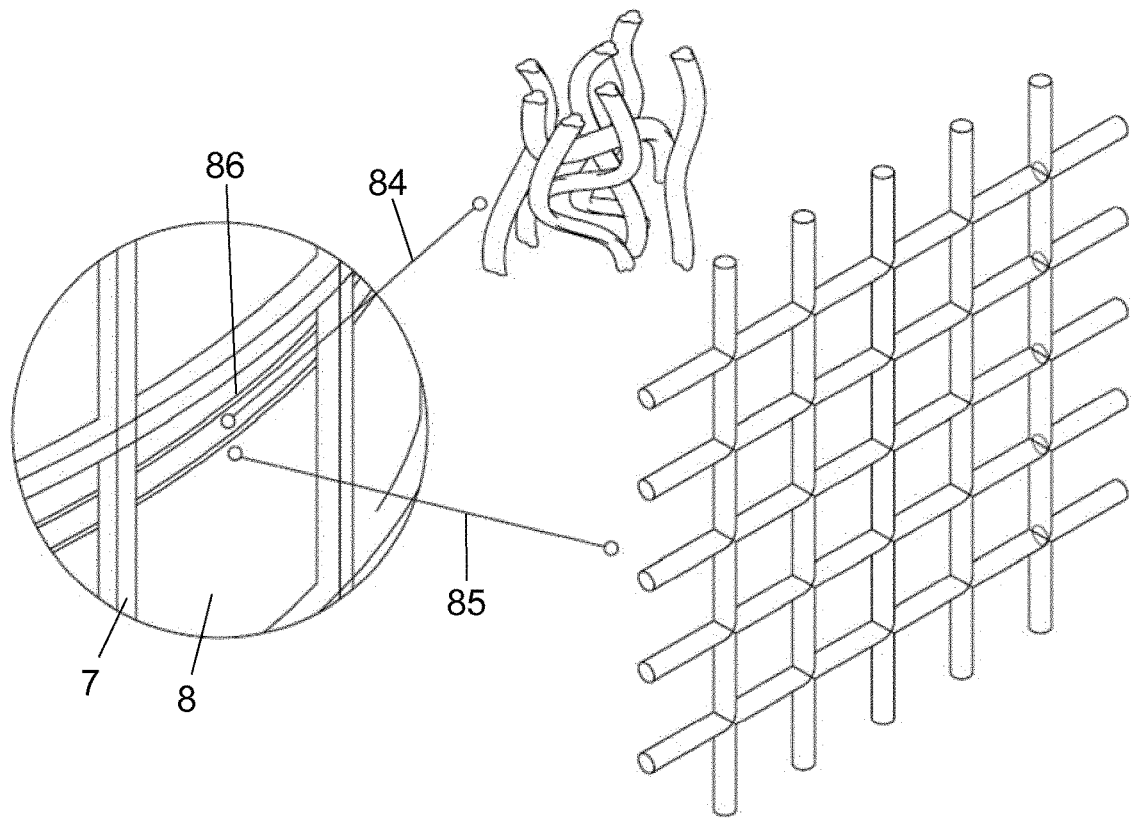
FIG. 5B is an enlarged detailed view of the area FIG. 5A that is encircled and marked with the letter T.

FIG. 5A shows another embodiment of the filter module 6 that can be used in connection with the blood-collecting canister shown in FIG. 1. For illustration purposes only, the filter material 8 of this embodiment of the filter module 6 is partially cut. The area that is encircled and marked with the letter T is depicted in an enlarged detailed view in FIG. 5B. In this detailed view, it can be seen that the filter material 8 comprises a prefiltering support layer 84 made up of non-woven fibers having a trilobal cross-section and a first mesh filter layer 85 that is arranged on the side of the prefiltering support layer 84 that faces the skeletal structure 7 of the filter module 6. Furthermore, the filter material 8 of this embodiment comprises a second mesh filter layer 86 that is arranged on the opposite side of the prefiltering support layer 84 than the first mesh filter layer 85. Thus, the prefiltering support layer 84 is encompassed between the first mesh filter layer 85 and the second mesh filter layer 86 and thus forms a sandwich-like structure together with the first mesh filter layer 85 and the second mesh filter layer 86.

Figure 6:
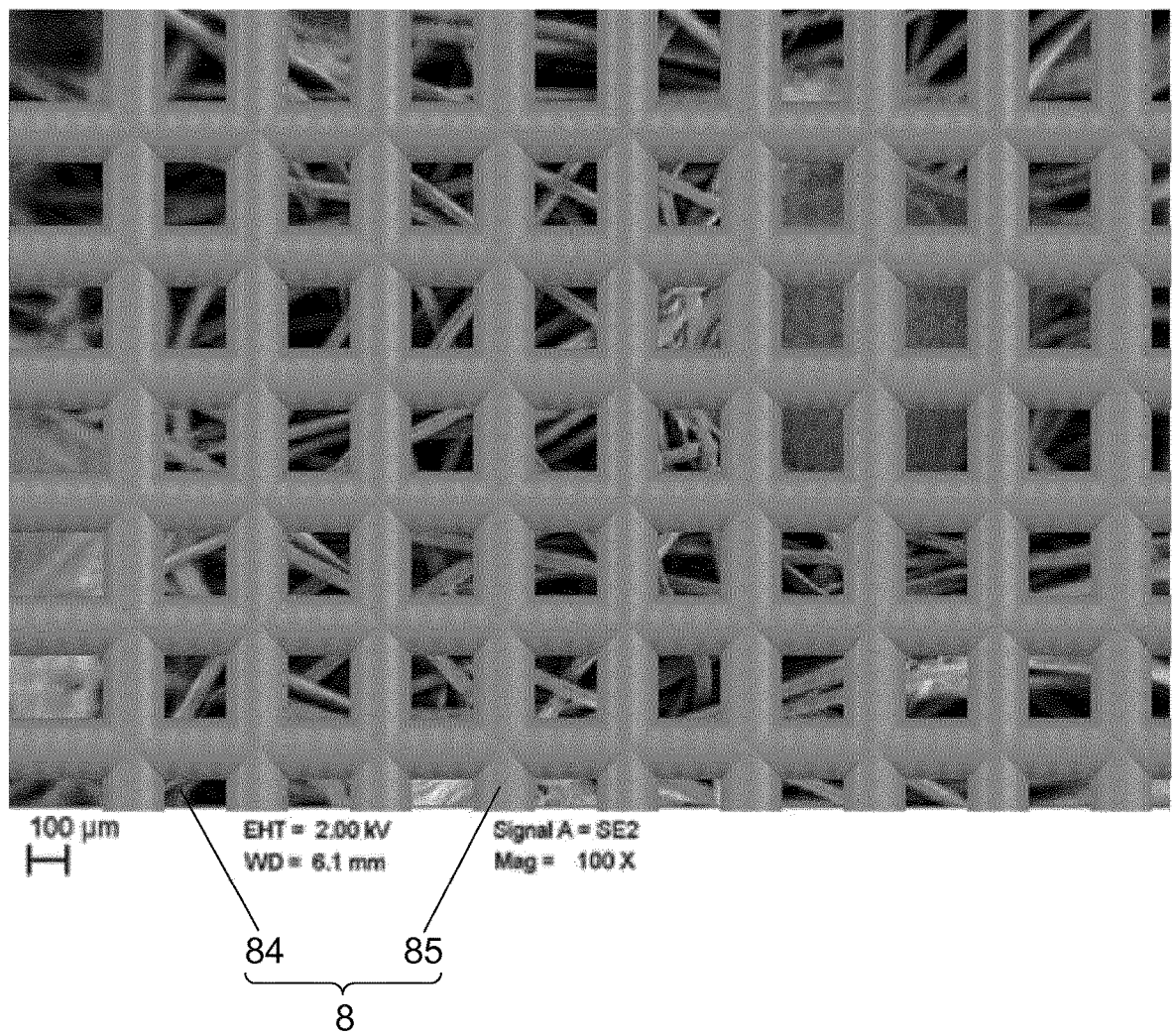
FIG. 6 is a schematic depiction of the microstructure of a prefiltering support layer and an mesh filter layer of an embodiment a filter assembly.

FIG. 6 shows a depiction of the microstructure of the filter material 8 based on an electron microscopic picture of individual fibers that make up the prefiltering support layer 84. In contrast to a non-woven and typically unordered structure of the individual fibers making up the prefiltering support layer 84, the individual grid elements that make up the mesh filter layer 85 are highly ordered and are arranged horizontally and vertically so as to form an ordered grid. In doing so, a highly repetitive and reproducible structure of the mesh filter layer 85 results.

Figure 7:
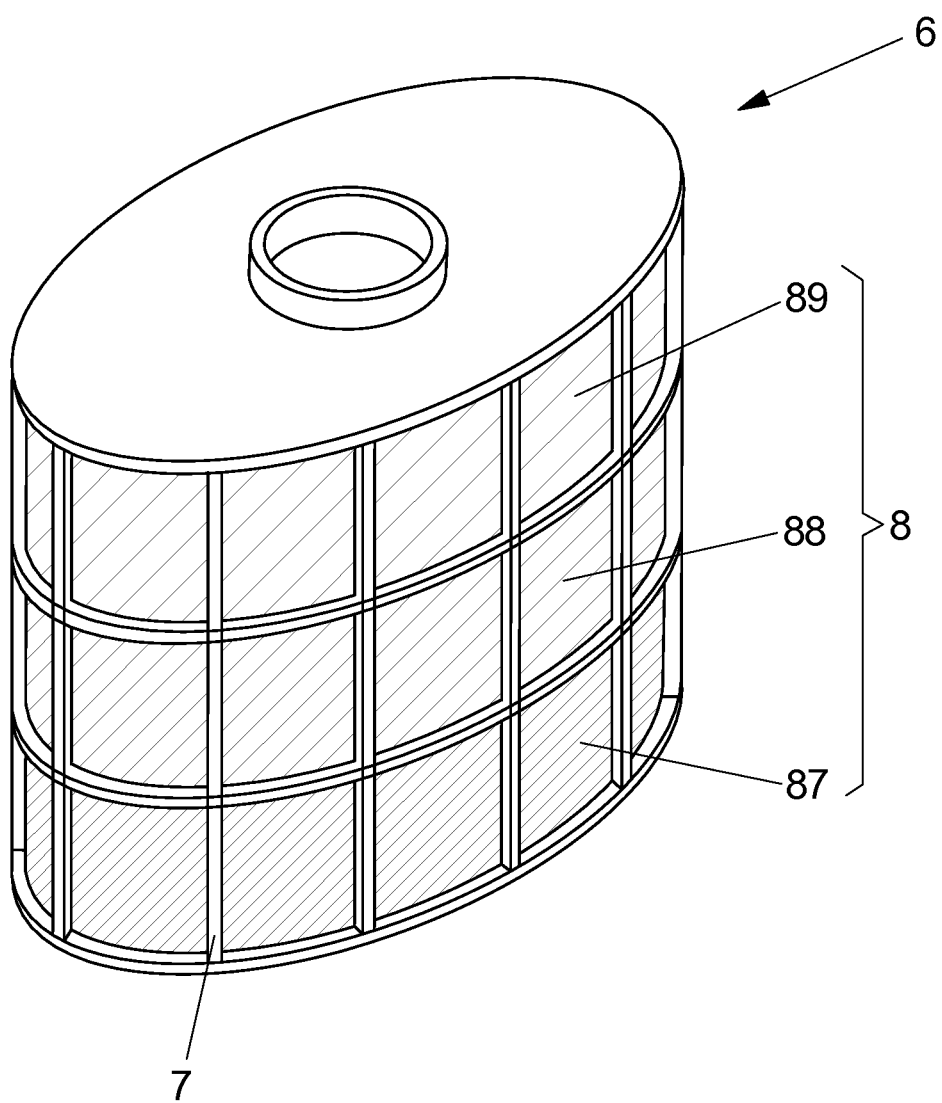
FIG. 7 is a schematic depiction of another embodiment of a filter assembly.

FIG. 7 shows another embodiment of a filter module 6 that can be used as filter module for the blood collection canister shown in FIG. 1. As the other embodiments of filter modules shown in the Figures discussed above, the filter module 6 of FIG. 7 comprises a skeletal structure 7 and a filter material 8. This filter material 8 comprises three zones of differing filtration capacity that are arranged one above another in a vertical extension direction of the filter module in which the filter module 6 is vertically aligned during normal operation. The lowest zone 87 has a mesh size of 40 μm so as to allow only particles having a size smaller than 40 μm to pass. An intermediate zone 88 has a mesh size of 80 μm and has a somewhat lower filtration capacity than the lowest zone 87 but and enables a higher volume to pass at the same time than the first zone 87. All three zones extend along the whole circumference of the filter module 6, i.e., along the whole circumference in a horizontal extension direction which is horizontally aligned during normal operation of the filter module 6.

The topmost zone 89 has a mesh size of 120 μm and allows an even higher blood flow through the filter material 8 than the intermediate zone 88 if the blood level in the filter material 8 is so high that blood can flow through the topmost zone 89. Thus, the filter material 8 has, in this embodiment, a vertical gradient of mesh size that efficiently prevents an overflow of the filter module 6 since it allows higher volumes of blood to pass the filter material 8 in dependence on the level or the amount of blood being present in the interior of the filter module 6. The topmost zone 89 can also be seen as a safety zone that allows proper functioning of the filter module 6 even in cases of a high blood inflow. As a side effect, the filtration effect is reduced in cases of such high blood inflow into the filter module 6, since the filtration capacity of the topmost zone 89 is significantly lower than the filtration capacity of the lowest zone 87.

The differing filtration capacities of the individual zones 87, 88 and 89 of the filter material 8 are achieved, in the embodiment of FIG. 7, by combining meshes having different mesh sizes onto one and the same prefiltering support layer. This significantly facilitates the manufacturing of the filter material 8 and does not necessitate an adjustment of the structure of the non-woven fibers making up the prefiltering support layer (which is not visible in the drawing of FIG. 7).

What is claimed is:

1. Filter assembly comprising a prefiltering support layer and a first mesh filter layer arranged downstream of the prefiltering support layer, wherein the prefiltering support layer comprises a non-woven fabric of fibers, the non-woven fabric having a pore size, wherein the first mesh filter layer comprises ordered grid elements and has a first mesh size, wherein the pore size of the prefiltering support layer is equal to or bigger than the first mesh size of the first mesh filter, and wherein the filter assembly comprises a filter holder arranged downstream the first mesh filter layer, wherein the filter holder contacts and stabilizes both the prefiltering support layer and the first mesh filter layer, and wherein the prefiltering support layer, the first mesh filter layer and optionally a second mesh filter layer extend over a vertical extension direction and over a horizontal extension direction and at least the non-woven fabric of the prefiltering support layer and the first mesh filter layer has a first area in a first height of the vertical extension direction and a second area in a second height of the vertical extension direction, wherein the first area and the second area have different pore or mesh sizes and exhibit different filtration capacities.

2. Filter assembly according to claim 1, wherein the filter holder is made from plastic and is overmolded over a part of the prefiltering support layer and a part of the first mesh filter layer.

3. Filter assembly according to claim 1, wherein the filter assembly comprises a second mesh filter layer arranged upstream the prefiltering support layer, wherein the second mesh filter layer has a second uniform mesh size, and wherein the second uniform mesh size of the second mesh filter layer is equal to or bigger than the pore size of the prefiltering support layer.

4. Filter assembly according to claim 1, wherein the prefiltering support layer comprises a spunbond nonwoven fabric.

5. Filter assembly according to claim 1, wherein at least a part of the fibers of prefiltering support layer each comprise at least one groove extending in the longitudinal direction of the respective fiber.

6. Filter assembly according to claim 1, wherein at least a part of the fibers have a lobate cross-section.

7. Filter assembly according to claim 1, wherein the prefiltering support layer, first mesh filter layer and second mesh filter layer have at least two areas of different pore or mesh sizes with different filtration capacities.

8. Filter assembly according to claim 1, wherein the vertical extension direction is vertically aligned during normal operation of the filter assembly and the horizontal extension direction is horizontally aligned during normal operation of the filter assembly.

9. Filter assembly according to claim 8, wherein at least one of the first area and the second area extend along the whole horizontal extension direction.

10. Filter assembly according to claim 1, wherein the filter assembly is free of anti-foam agents.

11. Filter assembly according to claim 1 for filtering a body fluid in vitro.

12. Filter assembly according to claim 11, wherein the body fluid is blood.

13. Filter assembly according to claim 6, wherein the fibers have a trilobal cross-section.

* * * * *